US008126546B2

(12) United States Patent
Williamson

(10) Patent No.: US 8,126,546 B2
(45) Date of Patent: Feb. 28, 2012

(54) ANODAL EXCITATION OF TISSUE

(75) Inventor: Richard Williamson, Santa Monica, CA (US)

(73) Assignee: Pacesetter, Inc., Sylmar, CA (US)

( * ) Notice: Subject to any disclaimer, the term of this patent is extended or adjusted under 35 U.S.C. 154(b) by 388 days.

(21) Appl. No.: 12/495,428

(22) Filed: Jun. 30, 2009

(65) Prior Publication Data

US 2010/0331906 A1    Dec. 30, 2010

(51) Int. Cl.
*A61N 1/00* (2006.01)
(52) U.S. Cl. .......................................................... 607/2
(58) Field of Classification Search ................ 607/2, 9, 607/7, 28, 17, 127, 116
See application file for complete search history.

(56) References Cited

U.S. PATENT DOCUMENTS

| 4,641,656 A | 2/1987 | Smits |
| 4,708,142 A | 11/1987 | DeCote, Jr. |
| 4,712,555 A | 12/1987 | Thornander et al. |
| 4,788,980 A | 12/1988 | Mann et al. |
| 4,809,697 A | 3/1989 | Causey, III et al. |
| 4,817,605 A | 4/1989 | Sholder |
| 4,932,407 A | 6/1990 | Williams |
| 4,940,052 A | 7/1990 | Mann et al. |
| 4,944,298 A | 7/1990 | Sholder |
| 4,944,299 A | 7/1990 | Silvian |
| 5,466,254 A | 11/1995 | Helland |
| 5,476,485 A | 12/1995 | Weinberg et al. |
| 5,522,855 A | 6/1996 | Hoegnelid |
| 5,573,550 A | 11/1996 | Zadeh et al. |
| 5,685,315 A | 11/1997 | McClure et al. |
| 5,720,768 A | 2/1998 | Verboven-Nelissen |
| 5,766,225 A | 6/1998 | Kramm |
| 5,766,229 A | 6/1998 | Bornzin |
| 5,814,079 A | 9/1998 | Kieval |
| 5,902,325 A | 5/1999 | Condie et al. |
| 6,070,100 A | 5/2000 | Bakels et al. |
| 6,122,545 A | 9/2000 | Struble et al. |
| 6,128,535 A | 10/2000 | Maarse |
| 6,169,921 B1 | 1/2001 | KenKnight et al. |
| 6,181,968 B1 | 1/2001 | Limousin |
| 6,198,967 B1 * | 3/2001 | Brewer et al. .................... 607/7 |
| 6,208,895 B1 | 3/2001 | Sullivan et al. |

(Continued)

FOREIGN PATENT DOCUMENTS

WO            9929368            6/1999

(Continued)

OTHER PUBLICATIONS

Lloyd, Michael S. MD et al., "Reverse Polarity Pacing: The Hemodynamic Benefit of Anodal Currents at Lead Tips for Cardiac Resynchronization Therapy," J Cardiovasc Electrophysiol. Nov. 2007;18:1167-1171.

(Continued)

*Primary Examiner* — George Manuel
*Assistant Examiner* — Robert Wieland

(57) ABSTRACT

A cardiac stimulation device has a plurality of electrodes that deliver therapeutic electrical stimulation to the heart. At least one electrode is designated a cathode that cathodically induces depolarization of the surrounding heart tissue. At least one electrode is designated an anode. The device is configured, through one or more of electrode size, electrode configuration, electrode arrangement, cathode/anode number and pulse delivery circuitry, to induce depolarization of the heart tissue in the area of the at least one anode electrode, thereby resulting in greater depolarization of the heart tissue with reduced power consumption.

7 Claims, 8 Drawing Sheets

U.S. PATENT DOCUMENTS

| | | |
|---|---|---|
| 6,278,894 B1 | 8/2001 | Salo et al. |
| 6,295,470 B1 | 9/2001 | Mower |
| 6,456,878 B1 | 9/2002 | Yerich et al. |
| 6,473,645 B1 | 10/2002 | Levine |
| 6,611,712 B2 | 8/2003 | Spinelli et al. |
| 6,687,545 B1 | 2/2004 | Lu |
| 7,110,815 B2 | 9/2006 | Heil, Jr. et al. |
| 7,191,003 B2 | 3/2007 | Greenhut et al. |
| 2002/0078968 A1 | 6/2002 | Spinelli et al. |
| 2003/0191502 A1* | 10/2003 | Sharma et al. ............. 607/9 |
| 2004/0030359 A1 | 2/2004 | Spinelli et al. |
| 2005/0277993 A1 | 12/2005 | Mower |
| 2007/0239215 A1 | 10/2007 | Bhunia et al. |
| 2008/0243196 A1* | 10/2008 | Libbus et al. ............. 607/2 |
| 2011/0152988 A1* | 6/2011 | Whitehurst et al. ........ 607/116 |

FOREIGN PATENT DOCUMENTS

| | | |
|---|---|---|
| WO | 2007086782 A1 | 8/2007 |

OTHER PUBLICATIONS

Thakral, Anshul et al., "Effects of anodal vs. cathodal pacing on the mechanical performance of the isolated rabbit heart," J Appl Physiol. 2000;89:1159-1164.

Thakor, Nitish PhD et al., "Effect of Varying Pacing Waveform Shapes on Propagation and Hemodynamics in the Rabbit Heart," Am J Cardiol 1997;79(6A):36-43.

* cited by examiner

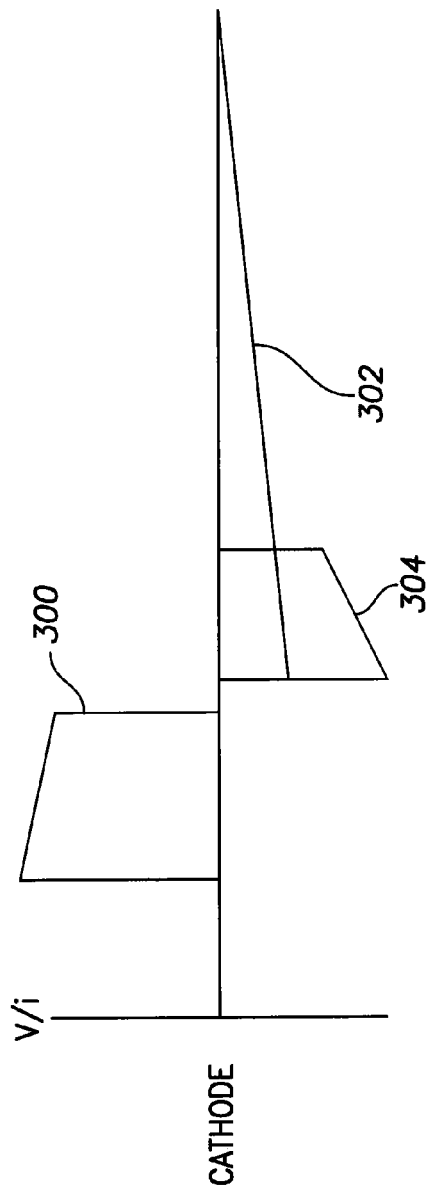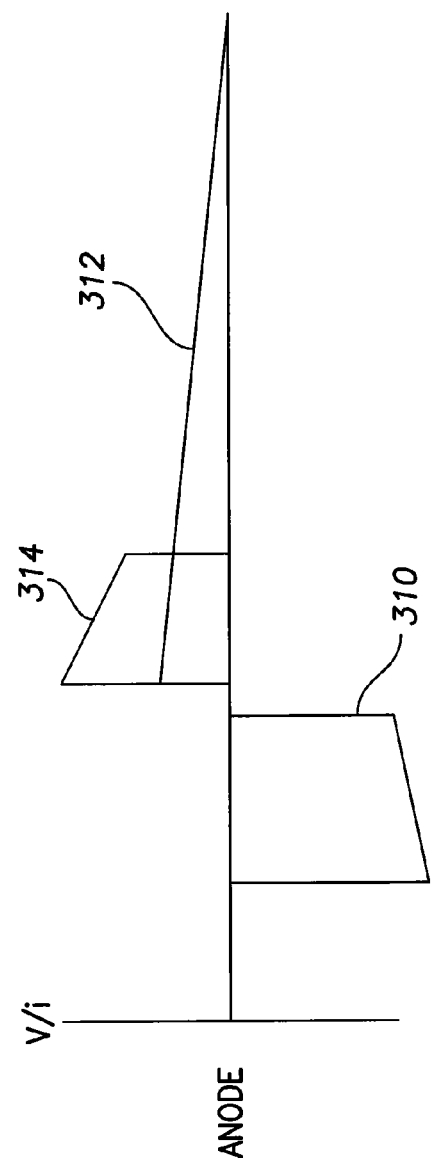

ANODAL EXCITATION OF TISSUE

CROSS-REFERENCE TO RELATED APPLICATIONS

This application contains subject matter related to copending U.S. patent application Ser. No. 12/267,941, filed Nov. 10, 2008, titled "Enhanced Hemodynamics Through Energy-Efficient Anodal Pacing" and U.S. patent application Ser. No. 11/961,720, filed Dec. 20, 2007, titled "Method and Apparatus with Anodal Capture Monitoring."

FIELD OF THE INVENTION

The present invention relates to cardiac stimulation devices, such as pacemakers, and, in particular concerns a cardiac stimulation device that uses anodal stimulation of cardiac tissue to enhance the delivery of therapy to patients.

BACKGROUND OF THE INVENTION

Implantable cardiac stimulation devices, such as Cardiac Resynchronization Therapy (CRT) devices are commonly used devices to treat cardiac arrhythmias. In general, these devices include an implantable control unit and a plurality of leads. The control unit has sensors and the leads can also function as sensors thereby allowing the control unit to receive signals indicative of the performance of the patient's heart and other parameters indicative of the patient's current physiologic state. Upon detecting the occurrence of a particular arrhythmia, an appropriate electrical therapy can be provided via the leads. In some instances, the appropriate therapy includes providing high voltage waveforms to the heart to terminate defibrillation or cardioversion in one or more of the chambers of the heart. In other instances, lower voltage pacing pulses are provided to one or more chambers of the heart to induce the heart to beat in a more regular fashion.

Over time these types of implantable cardiac stimulation devices have become increasingly more capable. One example of which is a CRT device that provides pacing pulses potentially to all four chambers of the heart in an effort to resynchronize the beating of the heart between the left and right hand sides of the heart and also between atria and ventricles. As is understood, after ischemic events, heart tissue may become damaged and electrical conduction within the chambers of the heart may be impeded. By positioning electrodes in both the left and right sides of the heart, for example in both the left and right ventricles of the heart, the heart can often be induced to beat in a more synchronized fashion thereby enhancing the hemodynamic performance of the heart.

One difficulty that occurs is that the tissue within the left ventricle is known to often have poor cardiac conduction. It is often dead or damaged after an ischemic event or may be otherwise diseased. When the tissue is dead, damaged or diseased, conduction within the tissue may be impeded thereby inhibiting the propagation of the electrical impulses which would cause the left ventricle to contract in a normal fashion. Additionally, the innervation of the muscular tissue of the heart can be blocked or damaged. In these cases, even though the muscular tissue is able to conduct normal, the pathway for the signals to synchronize the contraction of the tissue is damaged. Both cases can result in a contraction that is not appropriately synchronized, and has a compromised mechanical output.

To address this particular issue in the context, bi-ventricular pacing is used. The biventricular pacing uses multiple electrical foci to deliver electrical stimulation to the heart. It is believed that multiple left ventricular leads are better able to promote synchronous mechanical contractions. These contractions can be generated through synchronous multisite depolarization of the left ventricle. The multiple sites of stimulation can overcome the effects of dead, damaged or diseased tissue. This can result in the damaged tissue being bypassed resulting in more normal contractions of the heart.

While multiple leads may promote better therapy for a damaged heart, applying electrical stimulation to multiple leads results in an increase in the amount of energy being expended by the implanted cardiac stimulation device. As is understood, implanted cardiac stimulation devices generally are power limited, typically using a battery for energy storage. Increased energy consumption results in reduced device life expectancy. Depleted energy supplies can be dangerous to the patient as a result of the device being unable to continue to deliver therapy or, at a minimum, may require an invasive surgical procedure to replace the energy supply.

Generally, therapeutic pulses are delivered to heart tissue between an anode and a cathode of an electrical system. Generally, stimulation that results in depolarization of the heart tissue is provided via the cathode for cathodic stimulation. Applying cathodic stimulation in this manner to one additional electrode of an implanted cardiac stimulation device at, for example, a rate of 60 beats per minute, may result in the loss of one year of life from an exemplary intracardioverter defibrillator (ICD) or two years from an exemplary pacemaker.

Thus, while it is desirable to be able to provide stimulation pulses to a plurality of electrodes implanted within the heart, the more stimulation pulses that are provided the greater the drain is on the battery of the implanted cardiac stimulation device. Hence, there is a need for a process by which multiple electrodes implanted within a patient's heart can be stimulated but done so in such a manner that reduces the consumption of limited battery power.

SUMMARY OF THE INVENTION

In one implementation the aforementioned needs are satisfied by an implantable cardiac stimulation device comprising at least one lead adapted to be implanted adjacent the tissue of a heart, wherein the at least one lead defines a plurality of electrodes wherein at least one of the plurality of electrodes is designated a cathode and at least one of the plurality of electrodes is designated an anode. In this implementation, the stimulation device further comprises a controller that receives signals indicative of the heart function, wherein the controller induces the delivery of electrical stimulus to the heart via the cathode so as to induce depolarization of the heart tissue adjacent the cathode and wherein the anode is configured so as to anodally induce depolarization of the heart tissue adjacent the anode in response to the cathodically induced depolarization of heart tissue.

In another implementation the aforementioned needs are satisfied by an implantable cardiac stimulation device that includes a plurality of leads that are adapted to be positioned within the chambers of a patient's heart so as to deliver therapeutic electrical stimuli thereto, wherein each of the plurality of leads include a plurality of electrodes adapted to deliver the electrical stimuli so as to induce depolarization of heart tissue adjacent the plurality of electrodes. In this implementation the implantable device further includes a controller that induces the delivery of therapeutic electrical stimuli via at least one of the electrodes on the plurality of leads that is designated a cathode so as to cathodically induce depolarization of heart tissue adjacent the at least one electrode designated the cathode and wherein the delivery of therapeutic electrical stimuli via the at least one electrode results in anodally induced depolarization of heart tissue adjacent at least one electrode designated by the controller as an anode.

In yet another implementation the aforementioned needs are satisfied by a method of delivering therapeutic electrical stimuli to the heart of a patient, the method comprising implanting at least one lead having a plurality of electrodes adjacent the heart of the patient, designating at least one of the plurality of electrodes to be the cathode and at least one of the plurality of electrodes to be the anode, and delivering therapeutic electrical stimulation from the cathode so as to induce depolarization of the heart tissue adjacent the cathode and wherein the delivery of electrical stimulation from the cathode results in depolarization of the heart tissue adjacent the anode.

The foregoing advantages will become more apparent from the following description taken in conjunction with the accompanying drawings.

BRIEF DESCRIPTION OF THE DRAWINGS

FIGS. 3A and 3B are exemplary waveforms illustrating pacing pulses that are provided to an anode and a cathode of the stimulation device of FIG. 1.

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
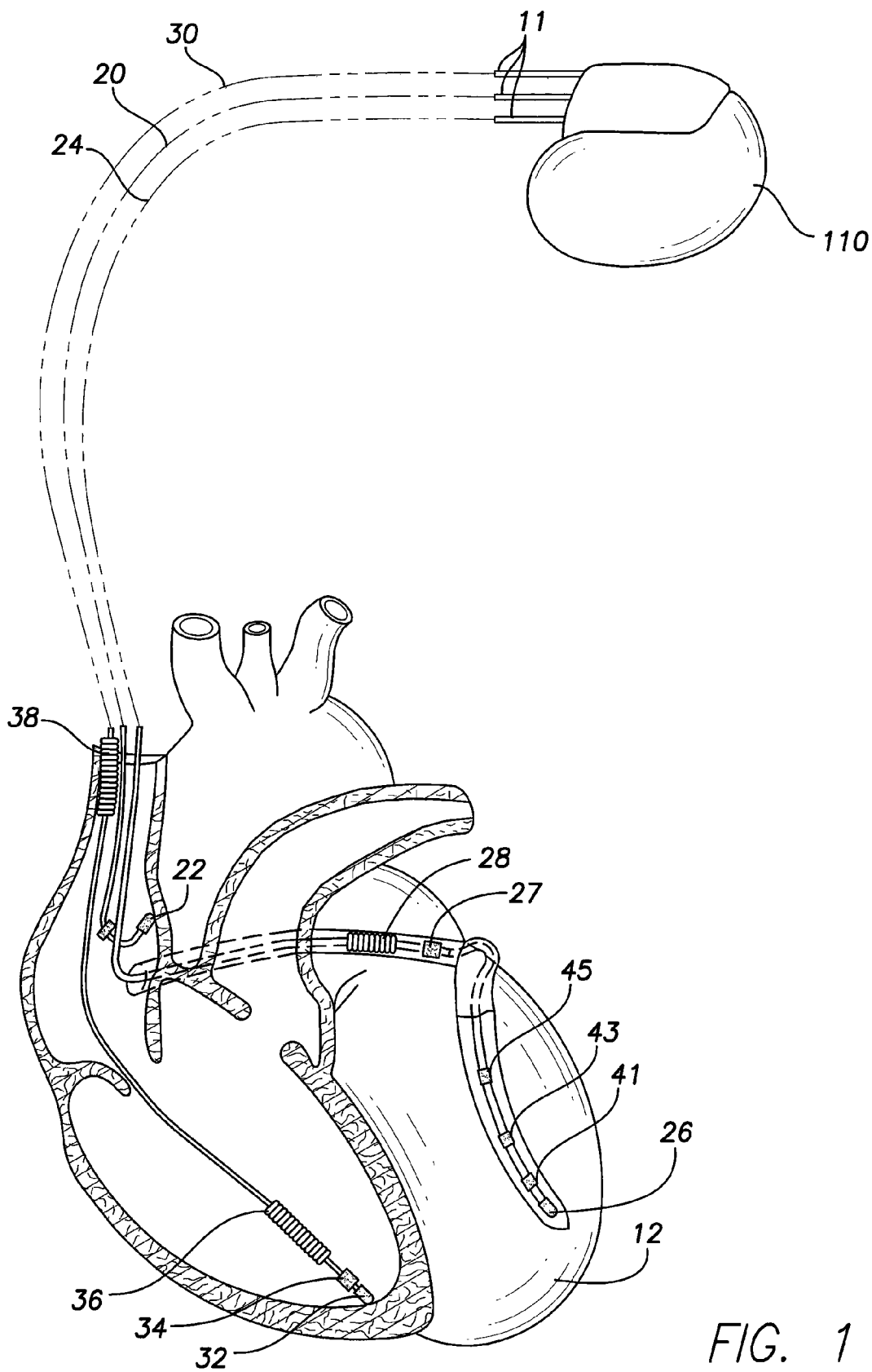
FIG. 1 is a simplified diagram illustrating an implantable stimulation device in electrical communication with a plurality of leads implanted into a patient's heart for delivering multi-chamber stimulation and shock therapy.

In one embodiment, as shown in FIG. 1, a device 10 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. As is also illustrated in FIG. 1, additional electrodes 41, 43, 45 may be distributed along the coronary sinus lead 24 in the left ventricle. As will be described in greater detail below, distributing additional electrodes within the left ventricle allows for more electrical foci for both cathodic or anodic stimulation of the surrounding tissue to thereby allow for more flexibility in providing cardiac resynchronization therapy to the heart via stimulation to multiple chambers of the heart. It will be appreciated that, while FIG. 1 illustrates a plurality of different electrodes on the coronary sinus lead 24, fewer or more electrodes can be accommodated without departing from the spirit of the present invention. Indeed, a single electrode may be used in unipolar applications without departing from the spirit of the present invention.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
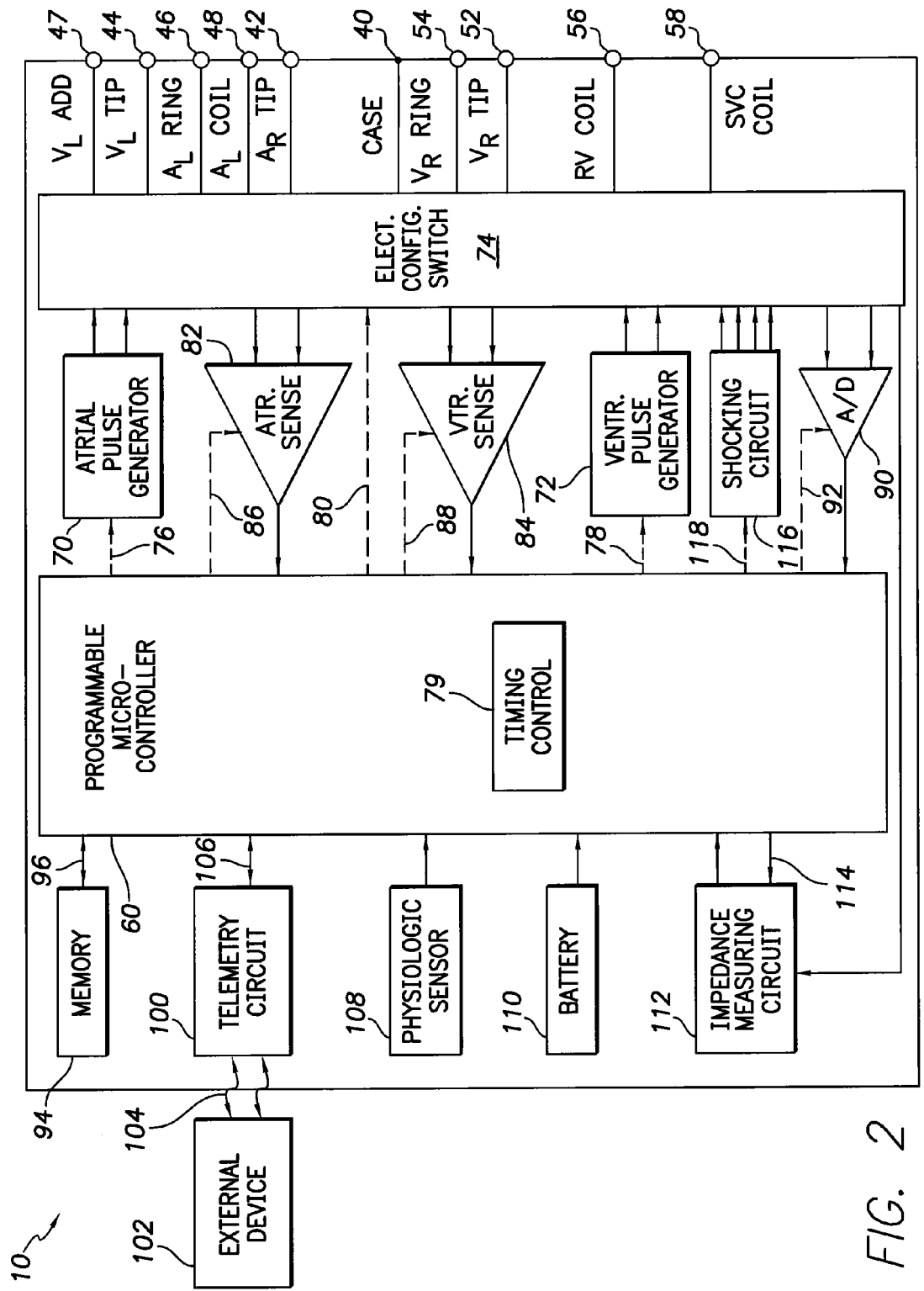
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

A housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively. Further, the connector includes one or more additional terminals ($V_L$ ADD) 47 associated with the additional electrodes 41, 43 and 45 positioned within the left ventricle discussed above.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial and ventricular sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. It will be appreciated that the the physiologics sensor might be within the casing of the implanted device or they might receive signals from the leads or there may be a sensing unit outside the casing that provides data to functional components within the casing. It will be appreciated that any of a number of different manners of data acquisition can be used without departing from the spirit of the present invention.

The stimulation device additionally includes a battery 110 which provides operating power to all of the circuits shown in FIG. 2. For the stimulation device 10, which employs shocking therapy, the battery 110 is generally capable of operating at low current drains for long periods of time and then be capable of providing high-current pulses (for capacitor charging) when the patient requires a shock pulse. The battery 110 generally also has a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monoflouride or a hybrid of the two.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it generally should detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Referring now to FIGS. 3A and 3B, exemplary waveforms of pacing pulses applied between electrodes are illustrated. As is understood, electrical stimulation 300 is applied between two electrodes within the heart with one electrode acting as the cathode which emits electrical charge into the surrounding heart tissue and the other electrode acting as the anode that receives the electrical charge. Generally, the electrical stimulation is applied between two electrodes and the resultant waveforms on the two electrodes 300, 310 are generally reciprocal to each other as shown in FIGS. 3A and 3B.

Depolarization of cardiac tissue can occur due to either cathodic stimulation or anodic stimulation. In general, prior art implantable cardiac stimulation devices configure the electrodes so that depolarization is provided through cathodic stimulation and potential anodic stimulation is suppressed. Generally, the current density at the anodal site with most cardiac stimulation devices is not high enough to elicit an anodal stimulation or depolarization of the surrounding tissue. Further, in many prior art applications, the electrode tip which forms the cathode often has a smaller surface area than the rings that define the return electrode. As such, the tip provides a higher current density at the cathode than at the anode.

Anodal stimulation can occur, however, as a result of either electrode make break effects or alternatively as the result of the electrically balancing repolarization signal of the lead comprising the anode. In this description, "anodal stimulation" refers to stimulation at the anode site either from the make break of the anodic pulse, or the cathodic repolarization effects as seen at the anode or any combination thereof.

As is shown in FIG. 3B, there is current energy being transmitted to the tissue surrounding the electrode functioning as the anode. This current density can be high enough to result in depolarization of the surrounding tissue. For implementations of the cardiac stimulation device 10 where stimulation is being applied cathodically at multiple sites, lower current density may be needed to achieve anodal stimulation at a particular site. Thus, it may be possible to stimulate heart tissue surrounding an anode using less power than if the same tissue was stimulated cathodically as the same power is being used to stimulate the tissue at the anode and the cathode simultaneously or near simultaneously.

A further advantage of selecting one or more sites to stimulate anodally is that the area of influence due to anodal current, which causes a virtual cathode, is often larger than the area of influence of cathodal current. Hence, in diseased tissue, the greater area of influence of the anodal current could promote less of a need for exact placement of the anode with respect to the excitable cardiac tissue. In some instances, this may relieve the need for more cathodes as the anodal area of stimulation is larger.

Figure 4A:
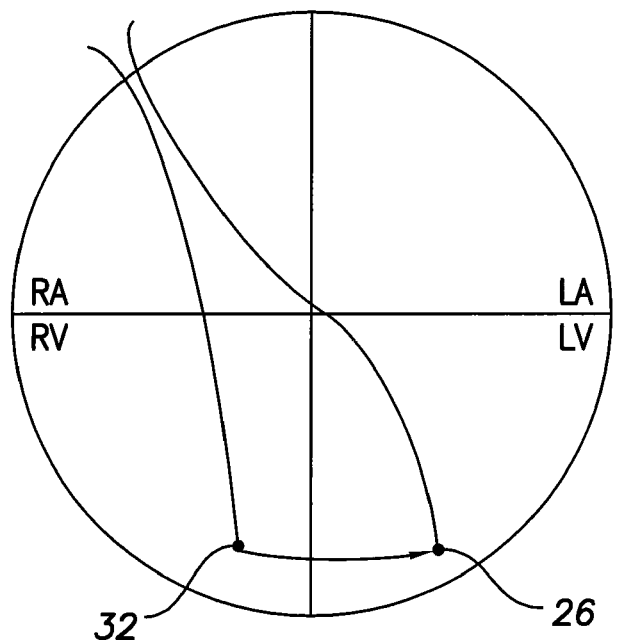
FIGS. 4A-4C are exemplary configurations of electrodes of the system of FIG. 1 wherein selected electrodes act as cathodes to stimulate regions of the heart and at least one selected electrode acts as an anode that is also adapted to stimulate the heart.
Figure 4B:
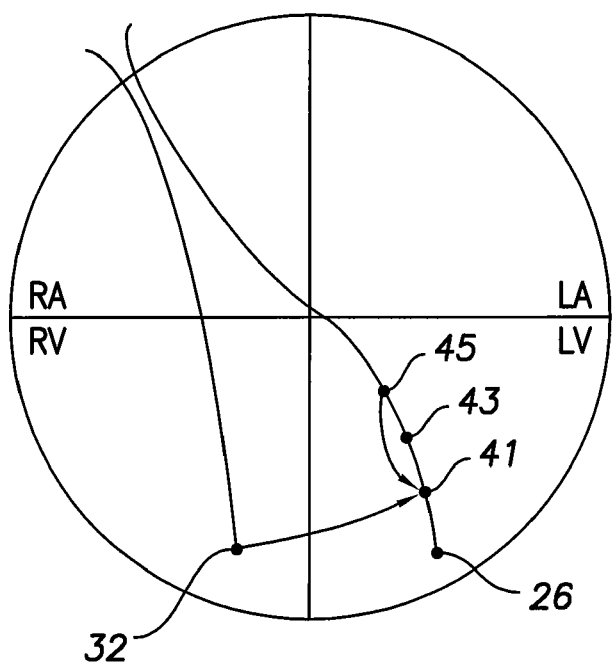
Figure 4C:
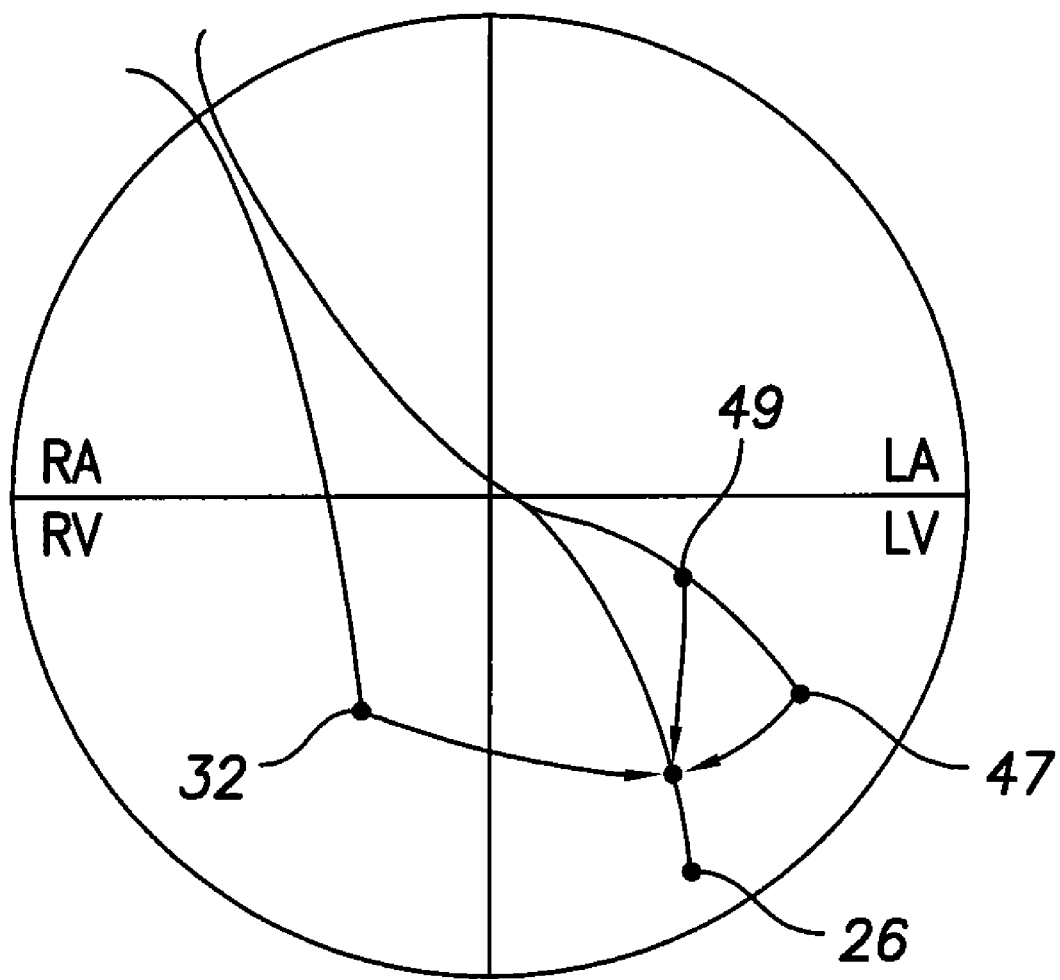

In one implementation, the three left ventricle ring electrodes 41, 43 and 45 (FIG. 1), may be reasonably placed in positions with respect to the cardiac tissue wherein anodal electrical stimulation could occur. The exact placement of the electrodes 41, 43, 45 or any of the other electrodes, as well as the shape and configuration of the electrodes may be varied to achieve a desired current density to induce anodal stimulation of the surrounding tissue. For example, the size of the anodal electrodes may be made smaller than the cathodal electrodes to increase current density at the anodal electrodes. FIGS. 4A-4C illustrate some exemplary configurations of electrodes which can result in anodal stimulation of tissue simultaneously with cathodic stimulation thereby achieving stimulation of more tissue of the heart without a consequent increase in the amount of battery power being used.

Referring to FIG. 4A, a simple two electrode example is shown. In this circumstance, the right ventricle RV tip electrode 32 (See, also FIG. 1) is designated as the cathode and the left ventricle LV tip electrode 26 is designated as the anode. Preferably, both electrodes 26, 32 are configured so as to be able to depolarize the tissue surrounding the electrodes. In this circumstance, only a single pulse between the two electrodes 26, 32 would be required to achieve depolarization at two distinct regions of the heart thereby resulting in greater tissue depolarization but achieving savings of power as compared to two cathodic stimulations.

As discussed above, the anode electrode may have to be configured to achieve the anodal stimulation of the heart tissue. In some implementations, the repolarization intervals could cause stimulation at the anodal site. Referring back to FIGS. 3A and 3B, an exemplary cathodal pulse 300 is applied via an electrode acting as a cathode which results in a corresponding anodal pulse 310 being applied to the heart tissue surrounding the anode. In some circumstances, the anodal pulse 310 may be insufficient to cause a depolarization of the heart tissue surrounding the anode.

As is also illustrated in FIGS. 3A and 3B, after the cathodal pulse 300 and anodal pulse 310 are applied, the cathode and anode exhibit repolarization phases 302 and 312 respectively. In the repolarization phase, the heart tissue is passively repolarizing and is thereby exhibiting an opposite electrical characteristic as seen by the cathode and anode respectively. In many implementations, the repolarization of the tissue surrounding the anode and the cathode is a slow, passive repolarization that is the result of the electrochemical mechanism of the cells of the surrounding tissue. The repolarization phases 302, 312 are exemplary passive repolarization phases where the repolarization of the cells occurs over a time period that is generally longer than the time period of the initial pacing pulse (e.g., pacing pulse of 0.5 ms with passive repolarization of 10-15 ms).

However, as is also illustrated in FIGS. 3A and 3B, additional energy can be supplied between the anode and cathode to increase the current density about the anode in order to enhance the potential of anodal stimulation. The curves 304, 314 on the cathode and anode respectively illustrate this circumstance. Active charge balancing, such as, for example, a FET driven balance of pacing current controlled by voltage observed on a charge balancing capacitor, can be used to achieve a quicker charge balancing, e.g., occurring within a time period equal to the pacing pulse e.g., 0.5 ms. This quicker charge balancing can result in sufficient current density at the anode to induce anodal stimulation of the surrounding tissue. This anodal stimulation will generally require less power from the battery due to the result of the previous depolarization of heart tissue.

FIG. 4B illustrate that more than one electrode can be designated as cathodes that provide pulses to heart tissue and a single electrode can be designated as receiving the energy from the two cathodes. In this exemplary implementation, the right ventricle tip electrode 32 and a left ventricle ring electrode 45 are designated as cathodes and another left ventricle ring electrode 41 is designated as the anode. In this circumstance, the current density that is being received by the electrode 41 is enhanced as a result of receiving energy from both the electrodes 32 and 45. This increase in current density may result in enhanced anodal stimulation at the electrode 41 thereby resulting in greater depolarization of the heart tissue within the left ventricle.

FIG. 4C illustrate that three sites of stimulation in the left ventricle can also be achieved. In this implementation, the right ventricle tip electrode 32 and two additional ring electrodes 49 and 47 can be used to stimulate a ring electrode 41. In this exemplary implementation, an additional lead or sublead has been positioned within the left ventricle so that the electrodes 47 and 49 are positioned in locations where localized depolarization is deemed to be desirable. Using more cathodes results in increased current density at the anode thereby resulting in increased ability to achieve anodal stimulation.

As will be understood from the discussion relating to FIGS. 4A-4C, any of a number of different combinations of electrodes can be designated the cathodes and the anodes to achieve a desired stimulation of the heart which includes anodal stimulation in the tissue surrounding at least one of the electrodes. The foregoing examples are simply exemplary examples of possible locations but the device 10 is flexible enough to allow a treating physician to select any of a number of different combinations of electrodes to achieve a desired resynchronization therapy.

Figure 5A:
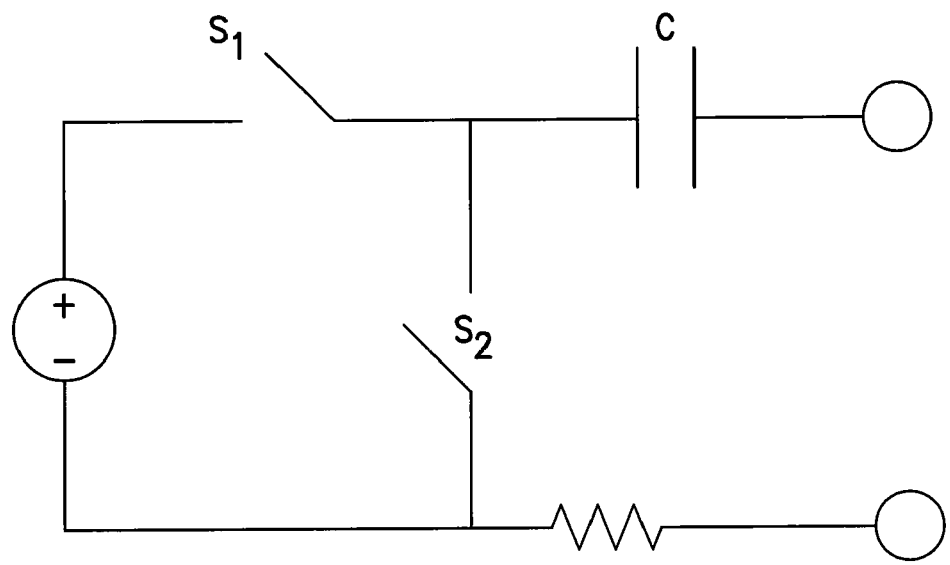
FIGS. 5A and B are, respectively, a simplified circuit diagram used in one embodiment to provide anodal and cathodal stimulation to the heart and a corresponding illustration of the waveform being provided.

FIG. 5A illustrates a simplified circuit for generating the anodal and cathodal stimulation pulses discussed above in conjunction with FIGS. 3A-3B. As discussed above, the electrical configuration switch 74 (FIG. 1) can be configured by the programmable microcontroller 60 to achieve variety of different equivalent circuits. For example, the switch 74 can be configured so that an equivalent circuit of FIG. 5A is achieved.

Figure 5B:
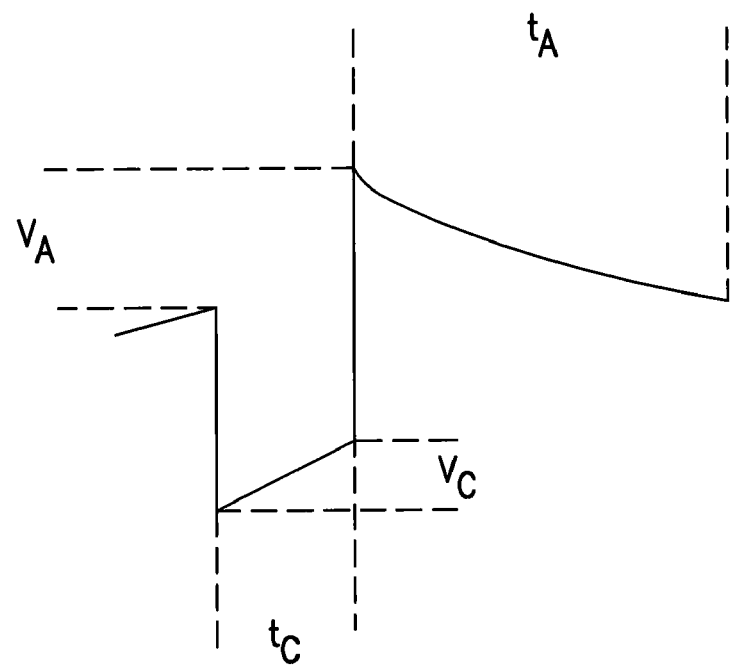

As shown, FIG. 5A provides a simplified circuit for providing a cathodal waveform followed by a passive anodal waveform. In this implementation, switch S1 and S2 are generally open. To provide the cathodal waveform, switch S1 is closed which provides the cathodal current pulse at the top electrode. After a desired time of delivery e.g., $t_c$ (FIG. 5B), the microcontroller 60 can then open Switch S1 to stop the cathode impulse. Subsequently, the microcontroller 60 can then close Switch S2 to passively balance the circuit thereby providing a passive anodal pulse over the time frame $t_A$ (FIG. 5B). The circuit of FIG. 5A, is simply exemplary of any of a number of different circuit that can be used to implement the anodal excitation of heart tissue without departing from the spirit of the present invention.

The circuit of FIG. 5A illustrates a circuit that allows anodal stimulation as a result of passive balancing of the circuit. As discussed above, it may be desirable to increase the current density at the anodal stimulation sites, to encourage anodal stimulation, by more actively balancing the circuit following the cathodal stimulation. The circuits of FIGS. 6A and 6B are exemplary circuit that perform this function that can be implemented by the configuration switch 74 and controller 60 (FIG. 1).

Figure 6A:
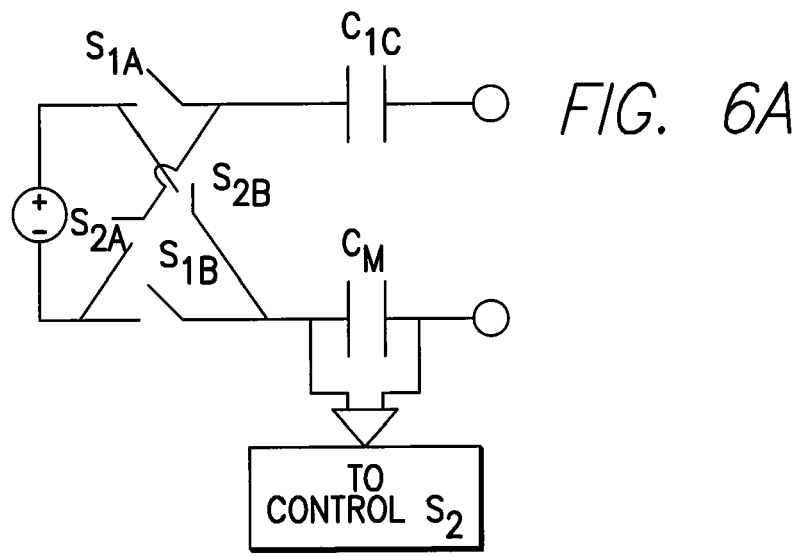
FIGS. 6A-6C are respectively, two simplified circuit diagrams used in other embodiments to provide anodal and cathodal stimulation to the heart and a corresponding illustration of the waveform being provided.
Figure 6B:
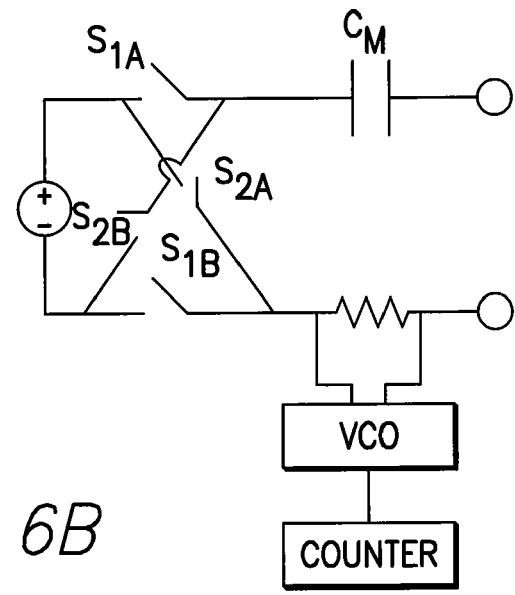
Figure 6C:
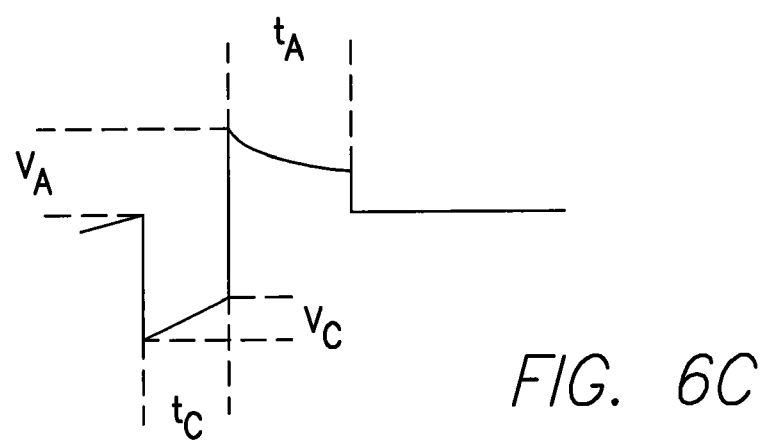

Referring specifically to FIG. 6A, as shown, there is a need to have a power source PS, that drives the current flow in the balancing phase. To achieve this, a second set of switches S2a and S2b are included. When no pacing pulse is being delivered, all of the switches S1a, S1b, S2a, S2b are open. To deliver the first cathodal phase of the pulse, the switches S1a and S1b are closed for a desired time period of $t_c$, which results in charge accumulating on capacitor $C_c$ and also results in the delivery of the cathodal pulse shown in FIG. 6C between the electrodes.

After the cathodal pulse has been delivered to the selected cathodal electrode, the switches S1a and S1b are opened and the switches S2a and S2b are closed thereby providing an anodal pulse to the selected anodal electrode. As shown in FIGS. 6A and B, the duration of the anodal pulse $t_A$, can be controlled in a number of different manners. Specifically referring to FIG. 6A, the switches S2a, S2b can be opened if the charge on a measurement capacitor $C_M$ is at a particular threshold, e.g., zero. Alternatively, referring to FIG. 6B, a resistor R can be sampled by a voltage controlled oscillator (VCO) and a counter to thereby determine the amount of energy has been provided through the anodal electrode. When the desired amount of energy has been delivered, the switches S2a, S2b can then be opened. In this way, the current being provided to the anodal electrode can be increased through dynamic recharging thereby inducing greater anodal stimulation of the tissue surrounding the electrode.

It will further be appreciated that a combination of both passive and active recharging can also be used without departing from the spirit of the present invention. For example, the switches S2a, S2b can be closed for a pre-selected period of time e.g., ½ of the cathodal phase $T_c$, and then these switches can be opened thereby allowing the overall circuit to balance passively. It will be appreciated that any of a number of different circuits can be used to implement or enhance anodal stimulation of the heart tissue without departing from the scope of the present invention.

Figure 7:
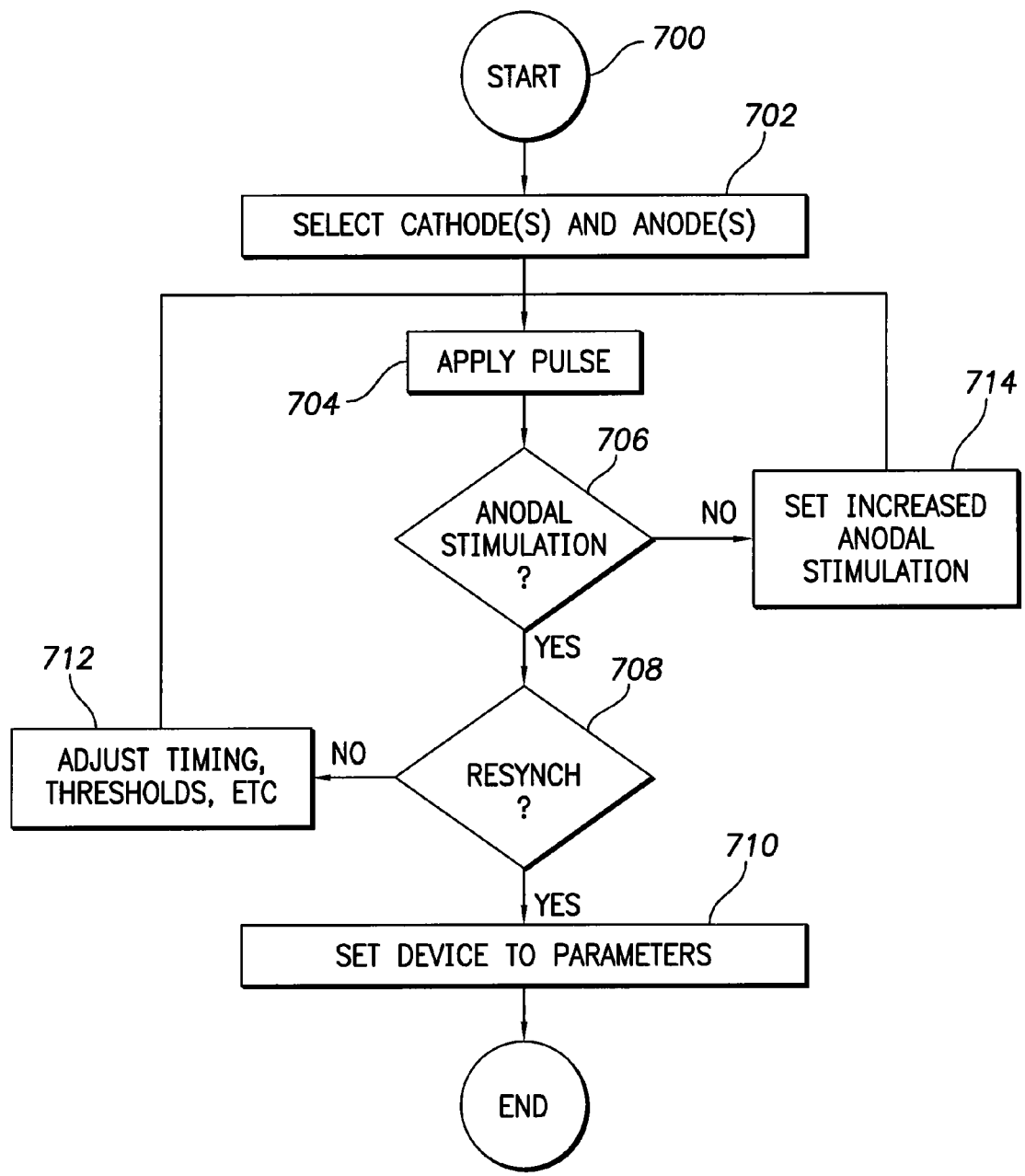
FIG. 7 is an exemplary flow chart illustrating a process by which cathodes and anodes can be selected for stimulation of regions of the heart.

FIG. 7 is an exemplary flowchart illustrating the process by which anodal stimulation can be selected to enhance resynchronization therapy that is being applied by the device 10. As shown, from a start state 700, a treating physician will select various electrodes to constitute anodes and cathodes in state 702. A pulse will then be applied in state 704 and the heart activity will be observed to determine whether there was anodal stimulation at the desired location in decision state 706. If no anodal stimulation occurred, then the configuration can be changed, in state 714, so that increased current density can be obtained at the anode site in the manner discussed above in conjunction with FIGS. 3A and 3B.

If anodal stimulation does occur, in conjunction with the cathodic stimulation, the treating physician can then ascertain whether a desired degree of resynchronization therapy is occurring in decision state 508. If the desired therapy is being applied, then the selected cathode and anode parameters can be then programmed into the processor so that the device will apply the appropriate therapy in state 510. Alternatively, the treating physician can, in state 512, alter the parameters such as timing of pulses and magnitude of pulses and various other thresholds until a desired resynchronization therapy is being applied.

Hence, the foregoing description provides a system and method of using anodal stimulation of heart tissue to achieve additional depolarization of the heart tissue for therapeutic purposes while using less energy from the battery. The exact configuration of cathodes and anodes will vary greatly from patient to patient and the exact therapy being provided can also vary greatly without departing from the spirit of the present invention.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable cardiac stimulation device comprising:
a plurality of electrodes adapted to be implanted adjacent the tissue of a heart, wherein at least two of the plurality of electrodes are respectively designated a first cathode and a second cathode, and at least one of the plurality of electrodes is designated an anode; and
a controller that induces the delivery of pacing stimuli to the heart via each of the first cathode and the second cathode, wherein each of the stimuli comprises a cathodal pulse sufficient to induce depolarization of the heart tissue adjacent its associated cathode, wherein each of the cathodal pulses induces a current density at the anode, wherein each current density, individually is insufficient to induce depolarization of the heart tissue adjacent the anode, however, the combination of both current densities is sufficient to induce depolarization of the heart tissue adjacent the anode.

2. The device of claim 1, further comprising a plurality of leads, each adapted to support one or more of the plurality of electrodes.

3. The device of claim 2, wherein the plurality of leads includes a right ventricular lead and a left ventricular lead each having a tip electrode and wherein the right ventricular tip electrode comprises one of the first cathode or the second cathode, and the left ventricular tip electrode comprises the anode.

4. The device of claim 2, wherein the plurality of leads includes a right ventricular lead and at least one left ventricular lead, wherein the left ventricular lead includes a plurality of spaced electrodes and wherein one of the plurality of spaced ring electrodes comprises the anode.

5. The device of claim 4, wherein an electrode on the right ventricular lead comprises the first cathode and at least one electrode on the left ventricular lead comprises the second cathode and wherein another one of the electrodes on the left ventricular lead comprises the anode.

6. A method of delivering therapeutic electrical stimuli to the heart of a patient, the method comprising:

designating at least two of a plurality of electrodes implanted adjacent the tissue of a heart a first cathode and a second cathode respectively, and at least one of the plurality of electrodes to be an anode; and delivering therapeutic electrical stimuli to the heart via each of the first cathode and the second cathode, wherein each of the stimuli comprises a cathodal pulse sufficient to induce depolarization of the heart tissue adjacent its associated cathode, wherein each of the cathodal pulses induces a current density at the anode, wherein each current density, individually is insufficient to induce depolarization of the heart tissue adjacent the anode, however, the combination of both current densities is sufficient to induce depolarization of the heart tissue adjacent the anode.

7. The device of claim 1 wherein the size of the anode electrode is smaller than the size of the first cathode electrode and the second cathode electrode.

* * * * *